US010018591B2

(12) United States Patent
Beisswenger

(10) Patent No.: US 10,018,591 B2
(45) Date of Patent: Jul. 10, 2018

(54) METHODS FOR IMPROVING DIABETES MANAGEMENT

(71) Applicant: PreventAGE HealthCare, LLC, Hanover, NH (US)

(72) Inventor: Paul J. Beisswenger, Hanover, NH (US)

(73) Assignee: PREVENTAGE HEALTHCARE, LLC, Lebanon, NH (US)

( * ) Notice: Subject to any disclaimer, the term of this patent is extended or adjusted under 35 U.S.C. 154(b) by 0 days.

(21) Appl. No.: 13/914,015

(22) Filed: Jun. 10, 2013

(65) Prior Publication Data
US 2013/0345175 A1 Dec. 26, 2013

Related U.S. Application Data

(60) Provisional application No. 61/658,218, filed on Jun. 11, 2012.

(51) Int. Cl.
*A61K 38/30* (2006.01)
*G01N 27/62* (2006.01)
*G01N 33/68* (2006.01)

(52) U.S. Cl.
CPC ......... *G01N 27/62* (2013.01); *G01N 33/6893* (2013.01); *G01N 2440/38* (2013.01); *G01N 2800/042* (2013.01)

(58) Field of Classification Search
CPC ... A61B 5/0075; G01N 2440/38; A61K 8/602
See application file for complete search history.

(56) References Cited

U.S. PATENT DOCUMENTS

| 6,323,038 | B1 | 11/2001 | Oya | |
|---|---|---|---|---|
| 2002/0002203 | A1* | 1/2002 | Rahbar | 514/561 |
| 2006/0240633 | A1* | 10/2006 | Martosella | C07K 1/16 438/348 |
| 2011/0079077 | A1 | 4/2011 | Lin | |

OTHER PUBLICATIONS

Thornalley et al., Biochem. J 375: 581-592, 2003.*
Ahmed, et al., "Assay of advanced glycation endproducts (AGEs): surveying AGEs by chromatographic assay with derivatization by 6-aminoquinolyl-N-hydroxysuccinimidyl-carbamate and application to Nepsilon-carboxymethyl-lysine- and Nepsilon-(1-carboxyethyl)lysine-modified albumin", Biochem J., 364(Pt 1):1-14(2002).
Ahmed, et al., "Degradation products of proteins damaged by glycation, oxidation and nitration in clinical type 1 diabetes", Diabetologia, 48:1590-1603 (2005).
Ahmed, et al., "Methylglyoxal-derived hydroimidazolone advanced glycation end-products of human lens proteins", Science, 44(12):5287-92 (2003).
Almuti, et al., "Effects of statins beyond lipid lowering: potential for clinical benefits", Intl J Cardiol.,, 109(1):7-15 (2006).

Baynes and Thrope, "Glycoxidation and lipoxidation in atherogenesis", Free Radic Biol Med., 28(12):1708-16 (2000).
Beisswenger, et al., "Metformin inhibition of glycation processes", Diabetes Metab., 29:6S95-103 (2003).
Beisswenger, et al., "Metformin reduces systemic methylglyoxal levels in type 2 diabetes", Diabetes, 48:198-202 (1999).
Beisswenger, et al., "Susceptibility to diabetic nephropathy is related to dicarbonyl and oxidative stress", Diabetes, 54: 3274-281 (2005).
Beisswenger, et al., "Increased collagen-linked pentosidine levels and advanced glycosylation end products in early diabetic nephropathy", J Clin Invest., 92(1):212-7 (1993).
Brownlee, "Glycation products and the pathogenesis of diabetic complications", Diabetes Care, 15(12):1835-43 (1992).
DCCT and UKPDS (DCCT/EDIC), "Effect of intensive therapy on the microvascular complications of type 1 diabetes mellitus", JAMA, 287(19):2563-9 (2002).
Degenhardt, et al., "Chemical modification of proteins by methylglyoxal", Cell Mol Biol., 44(7):1139-45 (1998).
Dyer, et al.,"Accumulation of Maillard reaction products in skin collagen in diabetes and aging", J. Clin. Invest., 91(6): 2463-9 (1993).
Geibauf, "Formation of N-formylkynurenine suggests the involvement of apolipoprotein B-100 centered tryptophan radicals in the initiation of LDL lipid peroxidation", FEBS Lett., 389:136-140 (1996).
Hammes, et al., "Benfotiamine blocks three major pathways of hyperglycemic damage and prevents experimental diabetic retinopathy", Nat Med., 9(3):294-9 (2003).
Hammes, et al., "Aminoguanidine treatment inhibits the development of experimental diabetic retinopathy", PNAS, 88:11555-8 (1991).
Hirsh, et al., "The reaction of some dicarbonyl sugars with aminoguanidine", Carbohyd. Res., 232:125-30 (1992).
Holman, et al., "10-year follow-up of intensive glucose control in type 2 diabetes", N Engl J Med., 359(15):1577-89 (2008).
Koschinsky, "Orally absorbed reactive glycation products (glycotoxins): an environmental risk factor in diabetic nephropathy", PNAS, 94(12):6474-9 (1997).
Lieuw-A-Fa, et al., Increased levels of N(epsilon)-(carboxymethyl)lysine and N(epsilon)-(carboxyethyl)lysine in type 1 diabetic patients with impaired renal function: correlation with markers of endothelial dysfunction, Neprol Dial Transplant., 19(3):631-6 (2004).

(Continued)

*Primary Examiner* — Gyan Chandra
(74) *Attorney, Agent, or Firm* — Prince Lobel Tye, LLP

(57) ABSTRACT

A method for determining the levels of biomarkers, specifically, advanced glycation end products (AGEs) and oxidation products (Ops) in a biological sample such as a plasma ultrafiltrate, is used to determine a patient's risk and/or rate of developing diabetes related nephropathy. The preferred biomarkers to measure include $N_\varepsilon$-(1-carboxyethyl-lysine (CEL), methylglyoxyl-derived hydroimidazolone (MGHI) and $N_\varepsilon$-carboxymethyllysine (CML). Also provided herein is a method of diabetic care which includes determining a diabetic patient's risk of developing diabetes related kidney disease and adjusting the patient's treatment regimen to include in addition to glucose lowering agents, additional treatments such as medications that modify the renin-angiotensin system, or specialized diets with low levels of AGEs or oxidative products.

21 Claims, 4 Drawing Sheets

(56) References Cited

OTHER PUBLICATIONS

Liu, et al., "Methylglyoxal induces apoptosis through activation of p38 mitogen-activated protein kinase in rat mesangial cells", Kidney Intl., 63:947-57 (2003).

Lo, et al., "Modification of plasma protein by methylglyoxal under physiological conditions. Prevention by aminoguanidine and L-arginine", Amino Acids, 5:172 (1993).

Lu, et al., "Increased plasma methylglyoxal level, inflammation, and vascular endothelial dysfunction in diabetic nephropathy", Clin. Biochem., 44(4):307-11 (2011).

Mauer, et al., "ACE-I and ARBs in early diabetic nephropathy", J Renin Angiotensin Aldosterone Sys., 3:262-9 (2002).

Mentink, et al., "Time course of specific AGEs during optimised glycaemic control in type 2 diabetes", Neth J Med., 64(1):10-6 (2006).

Monnier, et al., "Glycation products as markers and predictors of the progression of diabetic complications", Ann NY Acad Sci., 1043:567-81 (2005).

Monnier, et al., "The role of the amadori product in the complications of diabetes", Ann NY Acad Sci, 1126:81-8 (2008).

Nathan, et al., "Management of hyperglycemia in type 2 diabetes: a consensus algorithm for the initiation and adjustment of therapy: update regarding thiazolidinediones: a consensus statement from the American Diabetes Association and the European Association for the Study of Diabetes", Diabetes Care, 31(1):173-5 (2008).

Ogawa, et al., "Methylglyoxal is a predictor in type 2 diabetic patients of intima-media thickening and elevation of blood pressure", Hypertension, 56(3):471-6 (2010).

Perkins, et al., "Serum levels of advanced glycation endproducts and other markers of protein damage in early diabetic nephropathy in type 1 diabetes" PLoS One, 7(4):335655 (2012).

Rodbard, et al., "Should the recommendation of the American Association of Clinical Endocrinologists for a hemoglobin A1c target of 6.5% be modified? A critical reappraisal of recent studies of intensive glycemic control", Endocr Pract., 14(6):791-5 (2008).

Rosario, et al., "Lipids and diabetic nephropathy", Curr Diabs Rep., 6(6):455-62 (2006).

Scleicher, et al., "Increased accumulation of the glycoxidation product N(epsilon)-(carboxymethyl)lysine in human tissues in diabetes and aging", J Clin Invest., 99(3):457-68 (1997).

Sell, "2-aminoadipic acid is a marker of protein carbonyl oxidation in the aging human skin: effects of diabetes, renal failure and sepsis", Biochem J., 404(2):269-77 (2007).

Sell, et al., "Pentosidine: a molecular marker for the cumulative damage to proteins in diabetes, aging, and uremia", Diabetes Metab Rev., 7(4):239-51 (1991).

Thornalley, et al., "Quantitative screening of advanced glycation endproducts in cellular and extracellular proteins by tandem mass spectrometry", Biochem J, 375(Pt 3):581-92 (2003).

Yu, et al., "Advanced glycation end-products and methionine sulphoxide in skin collagen of patients with type 1 diabetes", Diabetologia, 49(10):2488-98 (2006).

Beisswenger, "Glycation and biomarkers of vascular complications of diabetes", Amino Acids, 42(4):1171-83 (2010).

Choudhuri, et al., "Role of N-µ-carboxy methyl lysine, advanced glycation end products and reactive oxygen species for the development of nonproliferative and proliferative retinopathy in type 2 diabetes mellitus", Mol. Vis., 19:100-113 (2013).

Fosmark, et al., "Increased serum levels of the specific advanced glycation end product methylglyoxal-derived hydroimidazolone are associated with retinopathy in patients with type 2 diabetes mellitus", Metabolism Clin. Experimental, 55(2):232-6 (2006).

Kilhovd, et al., "Increased serum levels of the specific AGE-compound methylglyoxal-derived hydroimidazolone in patients with type 2 diabetes", Metabolism Clin. Experimental, 52(2):163-7 (2003).

Pun, et al., "Pathological significance of mitochondrial glycation", Intl J Cell Biol., 19(3): 1-13 (2012).

Rabbani, et al., "Glycation of LDL by methylglyoxal increases arterial atherogenicity: a possible contributor to increased risk of cardiovascular disease in diabetes", Diabetes, 60(7): 1973-80 (2011).

Shcheglova, et al., "Reactive immunization suppresses advanced glycation and mitigates diabetic nephropathy", J Am Soc Nephrol., 20(5):1012-9 (2009).

Stitt, et al., "Diabetes-related adduct formation and retinopathy", J Ocul Bio Dis Infor., 4(1-2):10-8 (2011).

\* cited by examiner

METHODS FOR IMPROVING DIABETES MANAGEMENT

CROSS-REFERENCE TO RELATED APPLICATIONS

This application claims priority to U.S. Provisional Application No. 61/658,218, filed Jun. 11, 2012, entitled "Methods for Improving Diabetes Management" by Paul J. Beisswenger.

FIELD OF THE INVENTION

The invention encompasses methods for monitoring or determining the risk of diabetic nephropathy or an associated disorder in a subject and improving diabetes management.

BACKGROUND OF THE INVENTION

Diabetes mellitus (DM) affects more than 25.8 million people in the United States alone, i.e. 8.3% of the population. About 1.9 million people aged 20 years or older were newly diagnosed with diabetes in 2010. An estimated 79 million people aged 20 years or older are believed to have prediabetes, which constitutes 5% of adults aged 20 years or older and 50% of adults aged 65 years or older. National Diabetes Information Clearinghouse, National Diabetes Statistics, 2011.

Much of the morbidity and cost of diabetes management is attributable to long-term diabetes-related complications. For example, diabetes is the leading cause of kidney failure, non-traumatic lower limb amputations and new cases of blindness among adults. Diabetes is also a major cause of heart disease and stroke. After adjusting for population age and sex differences, average medical expenditures among people with diagnosed diabetes were 2.3 times higher than the expected expenditures without diabetes. The cost of diabetes in 2007 was $175 billion, which includes $116 billion in excess medical expenditures and $58 billion in reduced national productivity. Dall, et al., *Diabetes Care*, 31(3):596-615 (2008).

Based on the current incidence of diabetes and demographics, it has been projected that the number of Americans with diabetic retinopathy will triple to 16 million by 2050, and the major cause of the dramatic expansion in rates of end stage renal disease in this country is due to new cases of diabetic nephropathy. People with diabetes also have a dramatic increase in the risk of heart attack and stroke. It was primarily treatment of these devastating complications that drove the cost of caring for diabetes to $245 billion in 2012, a 45% increase since 2007.

The chronic elevation of blood glucose level associated with DM leads to damage of blood vessels. The resulting problems are grouped under "microvascular disease" (due to damage to small blood vessels) and "macrovascular disease" (due to damage to the arteries). The damage to small blood vessels leads to a microangiopathy, which can cause diabetic retinopathy and/or diabetic nephropathy. Microvascular complications including retinopathy and nephropathy account for the most prevalent and severe morbidity associated with diabetes and are involved in mediating the increased risk of cardio- and cerebrovascular disease as well. Diabetes is also the leading cause of renal insufficiency and end-stage renal disease (ESRD) in the U.S., and the Western world. Although diabetic microvascular complications are clearly associated with the degree of hyperglycemia, not all diabetic individuals with poor glycemic control develop renal or advanced retinal complications. Conversely, some diabetic patients develop severe complications despite well-controlled blood glucose concentrations.

It is distressing that there have been virtually no new biomarkers identified for the early detection of diabetic complications over the past 20-30 years, and the current biomarkers for identifying this "high-risk" subgroup continue to have significant limitations. A first sign for kidney damage is the presence of protein in urine (micro- or macroalbuminuria) which can be assessed by a clinical laboratory test or the latter with a simple dip stick test. The most common test used to date is still serum creatinine while acknowledging its missing accuracy. A limitation of tests relying on microalbuminuria, which occurs when kidney damage is already in place, is that it is only useful for detecting diabetic nephropathy at the asymptomatic stage. Early diagnostic or predictive tests would revolutionize diabetes management, because treatment strategies could be set in place to prevent or delay eventual diabetic nephropathy.

U.S. Pat. No. 6,323,038 discloses a pyridinium compound as a diagnostic reagent for detecting complications associated with diabetes or renal failure. U.S. Publication No. 2011/0079077 discloses urine and serum proteins and their fragments, which alone, or in combination, can be used to diagnose early stage diabetic nephropathy. The current biomarkers (i.e. measures of hyperglycemia) for identifying this "high-risk" subgroup have significant limitations. The Diabetes Control and Complications Trial (DCCT) showed that $HbA_{1c}$ (A1C) alone (i.e., levels of glycated hemoglobin) does not completely determine risk of outcomes. (Beisswenger, et al., *Diabetes*, 54: 3274-3281 (2005)). The "Natural History of Diabetic Nephropathy Study" has shown that only 9% of the risk of progressive glomerular basement membrane (GBM) thickening in type 1 diabetes is accounted for by the baseline A1C level. The biomarkers for progression of diabetic retinopathy (DR) and diabetic nephropathy (DN), including retinal morphological change or the appearance of albuminuria on regular examinations, are unable to identify those at greatest risk during the long 10-20 year "silent phase" when evolving or incipient damage to the kidney, eyes, and CV system is not clinically apparent (Nathan, et al, *New England Journal of Medicine*, 353(25): p. 2643-53 (2005)). By the time these markers become positive, substantial pericyte drop-out and avascular capillaries are frequently present in the retina (Ahmed, et al., *Biochem Soc Trans*, 31(Pt 6):1417-22 (2003), while substantial irreversible kidney damage can be present by the time microalbuminuria occurs (Nathan, et al., *New England Journal of Medicine*, 353(25):2643-53 (2005)). It is also widely recognized that CV disease may remain silent for many years, in spite of the gradual accumulation of serious and life-threatening lesions (Mauer, et al., *J. Renin-Angiotensin-Aldosterone System*, 3:262-269 (2002); Almuti, et al., *Int. J. of Cardiol.*, 109(1):7-15 (2006)). In addition, more aggressive treatment for DN with Ace inhibitors (ACEI) and Angiotensin receptor blockers (ARBs) instituted when albuminuria is detected, is unable to slow progression of structural glomerular lesions, as shown by the RASS (Koschinsky, et al., *Proc. Natl. Acad. Sci. USA*, 94(12):6474-6479 (1997)), suggesting that prevention in a highly susceptible individual is a far superior approach.

As a result of the inability to adequately predict a diabetic patient's risk of developing diabetes related complications, current clinical treatment decisions are made on the premise that all diabetic patients are equally susceptible to complications. This approach is limited, however, since only 50% of patients with type 2 diabetes achieve the recommended A1C treatment goal of <7% in a large population-based study (NHANES) (DCCT/EDIC, *JAMA*, 287(19):2563-9 (2002)), and the success rates are even lower in type 1 diabetes (Nathan, et al., *Diabetes Care*, 31(1):173-5 (2008); Holman, et al., *New England Journal of Medicine*, 359(15): 1577-89 (2008)). Reasons for this large-scale failure include the lack of patient specific predictive information, the overwhelming rates of newly discovered diabetes, the massive expense of providing adequate care, the lack of sufficient and adequately trained medical providers, and patient denial of the potential consequences of poor treatment compliance resulting from their lack of accurate individualized predictive information on risk. Diabetes treatments are not only expensive, but some are accompanied by a high-risk of hypoglycemia and drug side effects, as well as the expense and risk of new treatments such as pancreatic transplants and the evolving artificial pancreas. Based on these considerations, it will become increasingly difficult to apply these therapies to all patients with diabetes, without having better information on individual risk and benefit.

Advanced glycation end products (AGEs) and oxidation products (OPs) have been proposed as possible factors for diabetic complications. Until recently, however, knowledge of these products has been limited to the Early Glycation Products (EGPs), several oxidation end products, and a few AGEs. Most prior studies have measured limited numbers of AGEs (Yu, et al. *Diabetologia*, 49(10):2488-98 (2006); Monnier, et al., *Annals of the New York Academy of Sciences*, (2008); (Beisswenger, et al., *Journal of Clinical Investigation*, 92(1):212-7 (1993); Dyer, et al., *J. Clin. Invest.*, 91(6): 2463-9 (1993); Monnier, et al., *Annals of the New York Academy of Sciences*, 1043:567-581 (2005)), particularly pentosidine and carboxymethyllysine, or have focused on a few end-products that reflect oxidative stress (Yu, et al. *Diabetologia*, 49(10):2488-98 (2006); Baynes, et al., *Free Radical Biology & Medicine.*, 28(12):1708-16 (2000). A substantial number of these analyses have also been performed as semi quantitative immunoassays, which have generally not been validated against quantitative chemical analyses. Although some of these studies have shown correlations between blood levels of these products and complications (Monnier, et al., *Annals of the New York Academy of Sciences*, 1043:567-581 (2005)), none have validated their predictive value in large-scale controlled diabetes outcome studies. A recent study by Perkins, et al., *PLoS One*, 7(4):335655 (2012) measuring the levels of AGEs and oxidative markers in LC/MS/MS concluded that there was no correlation between any of the protein damage adduct residues of plasma protein nor concentration of related free adduct with subsequent early glomerular filtrate rate (GFR) that leads to end stage renal disease.

It is desirable to identify biomarkers that can be used to predict a patient's risk of developing diabetes related kidney disease before the patient exhibits known signs and/or markers of kidney disease or malfunction.

It is an object of the present invention to provide biomarkers useful for determining a diabetic subject's risk of developing kidney disease.

It is also an object of the present invention to provide a method for identifying a subject at risk of developing diabetes related kidney disease.

It is a further object of the present invention to provide a method for identifying a diabetic's risk of eye or cardiovascular disease.

SUMMARY OF THE INVENTION

A method for determining the levels of biomarkers, specifically, advanced glycation end products (AGEs) and oxidation products (OPs) in a biological sample, preferably plasma or plasma ultrafiltrate, or a urine sample, has been developed. The method is useful in detecting the levels of biomarkers such as $N_\varepsilon$-carboxy methyl-lysine (CML); $N_\varepsilon$-carboxy ethyl-lysine (CEL); Glyoxal hydroimidazolone (GH1); Methylglyoxal hydroimidazolone (MGH1); 3-Deoxyglucosone Hydroimidazolone (3DGH); methionine sulfoxide (MetSO); and 3-nitrotyrosine (3-NT), dityrosine, and 2-aminoadipic acid. The method of preparation of the samples is important. The biomarker levels in the sample are preferably determined by Liquid Chromatography/Triple Quadrupole Mass Spectroscopy (LC-MS/MS). In one preferred embodiment for measuring biomarkers using LC-MS/MS, the stationary phase is C18 with heptafluorobutyric acid being used as an ion pairing agent. This allows the analysis to be performed with a single column relative as opposed requiring 2 columns.

A method for determining a subject's risk of developing DN or a disorder associated with DN has also been developed. The method includes obtaining a test sample from a subject diagnosed with diabetes, measuring the levels of $N_\varepsilon$-(1-carboxyethyl-lysine (CEL), methylglyoxyl-derived hydroimidazolone (MGHI) and $N_\varepsilon$-carboxymethyllysine (CML) and comparing the values to the metabolite levels shown to be associated with either progression or non-progression of diabetic nephropathy.

Also provided is a method of diabetic care which includes determining a diabetic patient's risk of developing diabetes related kidney disease and adjusting the patient's treatment regimen to include, in addition to glucose lowering agents, additional treatments such as medications that modify the renin-angiotensin system, or specialized diets with low levels of AGEs or oxidative products, to delay or reduce the severity of kidney, eye or cardiovascular disease.

DETAILED DESCRIPTION OF THE INVENTION

I. Definitions

Figure 1:
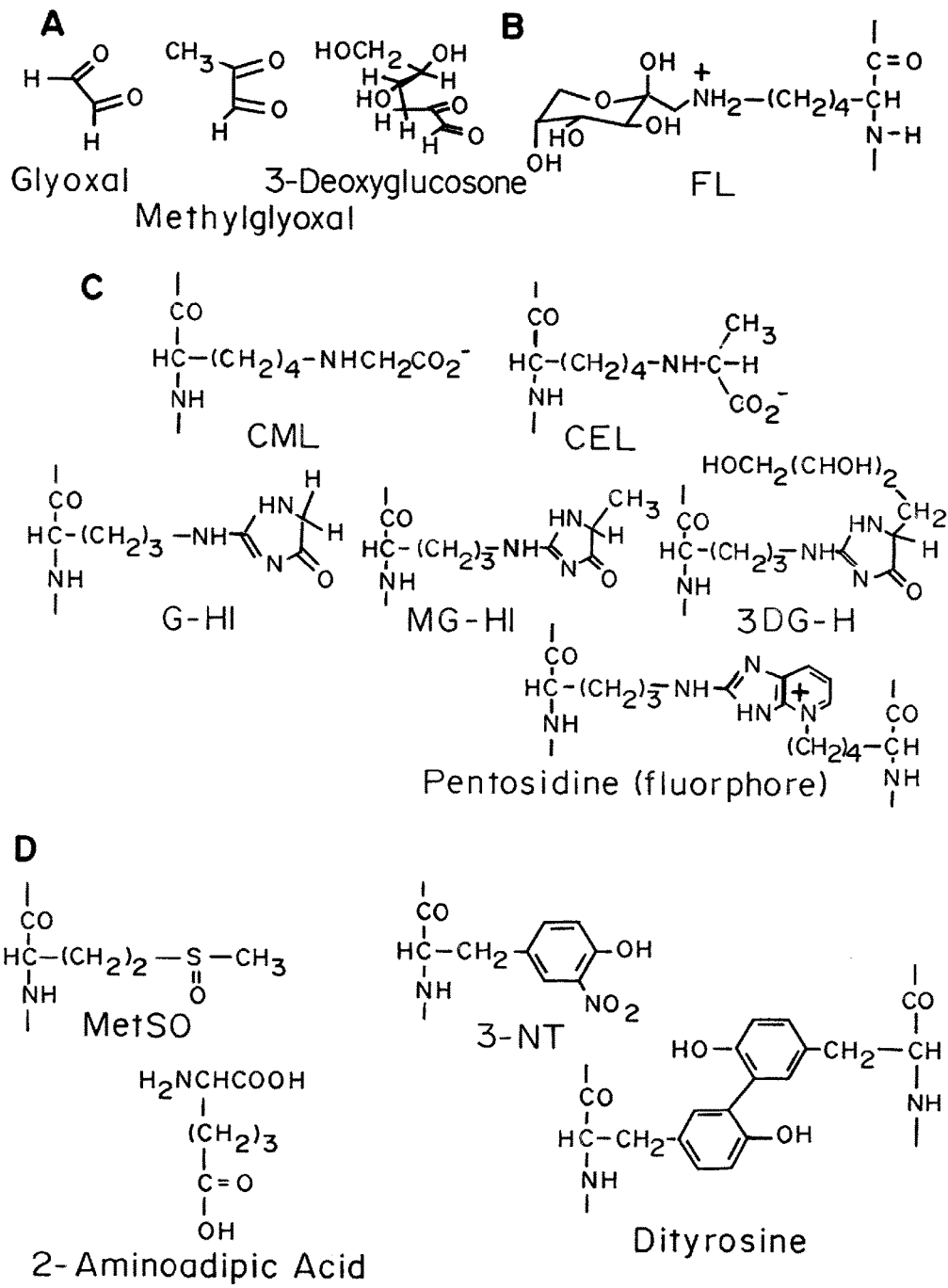
FIG. 1 shows the chemical structures of biomarkers. FL=$N_\varepsilon$-Fructosyllysine; CML=$N_\varepsilon$-carboxy methyl-lysine; CEL=$N_\varepsilon$-carboxy ethyl-lysine; G-H1=glyoxal hydroimidazolone; MG-H1=Methylglyoxal hydroimidazolone; 3DG-H=3-Deoxyglucosone Hydroimidazolone; MetSO=methionine sulfoxide; 3-NT=3-nitrotyrosine.

"A disorder associated with diabetic nephropathy" as used herein refers to a disorder that stems from angiopathy of capillaries in the kidney glomeruli. Non-limiting examples of associated disorders may include nephritic syndrome, chronic kidney failure, and end-stage kidney disease.

"Diabetic nephropathy" as used herein refers to a disorder characterized by angiopathy of capillaries in the kidney glomeruli. The term encompasses Kimmelstiel-Wilson syndrome, nodular diabetic glomerulosclerosis and intercapillary glomerulonephritis.

Type I diabetic individuals have a 20-40% risk of developing kidney disease.

The biomarkers described herein allow identification of this population so that those people who are identified have a 10-50%, or greater risk of developing diabetic nephropathy.

II. Method for Predicting a Patient's Risk of Developing Diabetic Nephropathy A. Markers to be Assessed Specific chemical end products have been identified in carefully documented outcome studies based on investigation of the activation of specific glycation and oxidative pathways in clinical populations with documented nephropathy and retinopathy. These pathways lead to the formation of a spectrum of early glycation products (EGPs), including the chemically reactive a dicarbonyl compounds, methylglyoxal (MG), 3-deoxyglucosone (3DG), and glyoxal (G). These α dicarbonyls, in turn, lead the formation of later stage chemical reactions to form advanced glycation end products (AGEs), a process that is independent from $HbA_{1c}$ formation. Increased glucose-induced oxidative stress (OS) may also be caused by inherent differences in processes that control cellular oxidative mechanisms, which can directly and independently activate major pathways that produce diabetic complications. It has been found that both dicarbonyl stress and OS are selectively activated in those prone to diabetic complications, resulting in higher levels of glycated and oxidized protein and lipid byproducts, but not directly to changes in $HbA_{1c}$.

Assays to assess blood and urine levels of selected glycation and oxidative end products of these chemical pathways have been developed to make the measurements more precise. Since these end products represent slowly turning over end-products of glycative and oxidative pathways, their use in clinical outcome studies should be superior to measurement of short acting chemical precursors which would not necessarily reflect long-term overproduction when checked in one or more blood and urine samples.

In these studies it was found that the quantitatively highest in vivo AGEs in type 1 diabetes are hydroimidazolones (HI) derived from arginine residues modified by methylglyoxal (MG), 3-deoxyglucosone (3DG), and glyoxal, produced in turn from their individual synthetic pathways. Other quantifiable AGEs in these studies include glyoxal-lysine derived carboxymethyl (CML), and the MG-lysine product, carboxyethyl-lysine (CEL). Markers of oxidation and nitration, including methionine sulfoxide (MetSO), formed by the oxidation of methionine, 2-aminoadipic acid formed from lysine residues, as well as other markers of nitrosive damage leading to production of 3-nitrotyrosine (3-NT) and dityrosine have also been measured. Substantial differences exist between diabetic and control populations (5 to 15 fold). The unprecedented increases observed in AGEs and OPs in diabetes, and the substantial differences observed between individuals, indicate that these biomarker levels, alone or in addition to HbA1c, have the potential to markedly sharpen the ability to differentiate subjects at very high versus very low risk of complications. The key AGEs and OPs that are most predictive of complications, including hydroimidazolones and MetSO, showed no correlation with $HbA_{1c}$, suggesting that they are produced by chemical pathways that relate to complications, but respond uniquely to the level of glycemia based on individual patient characteristics.

AGE and OP biomarkers are measured in plasma and urine samples to assess a person's risk of developing diabetic nephropathy or other complications. By comparing the levels in carefully defined nephropathy progressors and non-progressors, the levels of specific AGE's allow determination of a diabetic subject's risk of developing diabetes related DN or a disorder associated with DN. In a preferred embodiment, plasma filtrate levels of three AGEs, CM=$N_\varepsilon$-carboxy methyl-lysine; CEL=$N_\varepsilon$-carboxy ethyl-lysine; and MG-H1=Methylglyoxal hydroimidazolone, alone or in combination with HbA1c, are indicators of early progression of DN. In a more preferred embodiment, MG-H1 levels alone are an independent predictor of a subject's risk of developing DN.

The methods described herein can be used to quantify the following products, which are shown in FIG. 1:

Arginine derived AGEs: These biomarkers include the quantitatively important hydroimidazolones (HI); which are AGEs derived from arginine residues modified by glyoxal, MG, and 3-DG and include G-H1 (glyoxal hydroimidazolone), MG-H1 (Methylglyoxal hydroimidazolone), and 3DG-H (3-Deoxyglucosone Hydroimidazolone), respectively.

Lysine derived AGEs: Other important AGEs that can be measured are lysine-based and include glyoxal derived $N_\varepsilon$-carboxymethyl-lysine (CML), and MG derived $N_\varepsilon$-carboxyethyl-lysine (CEL) (Thornalley, et al., *Biochemical Journal*, 375(Pt 3):581-92 (2003)). Other AGEs that can be measured include the more traditional product, pentosidine, which is measured by HPLC and fluorescence detection (Sell, et al., *Diabetes*, 40(Suppl I):302A (1991)).

Quantitative markers of oxidative damage to proteins can also be measured and include methionine sulfoxide (MetSO), formed by the oxidation of the sulfhydryl group on Methionine (Yu, et al., *Diabetologia*, 49(10):2488-98 (2006)). The tyrosine cross-link, dityrosine, as well as a widely studied marker of combined oxidative/nitration damage to proteins, 3-nitrotyrosine (3-NT), can also be measured (Geibauf, *FEBS Letters*, 389:136-140 (1996)). To amplify the information obtained on the role of oxidative stress in the development of diabetic complications, another unique oxidative product, 2-aminoadipic acid, a product resulting from metal catalyzed oxidation of lysyl residues (Sell, *Biochemical J.*, 404(2):269-77 (2007)), can also be measured.

Urine creatinine levels can also be determined to provide uniform expression of product/creatinine urine analyte content. The urinary and serum "free fraction" determinations allow the calculation of renal clearance rates of each analyte.

Studies performed in landmark outcome studies with type 1 diabetes, are applicable to patients with type 2 diabetes as well. It is well recognized that major clinical trials have shown a similar significant relationships between glycemic control and progression of DN and DR in both type 1 and type 2 diabetes in DCCT and UKPDS (DCCT/EDIC, *JAMA*, 287(19):2563-9 (2002); Holman, et al., *New England Journal of Medicine*, 359(15):1577-89 (2008), suggesting similarities in pathogenesis for both diabetes types. These considerations have led the American Diabetes Association (ADA), American Association of Clinical Endocrinologists (AACE), and European association for the Study of Diabetes (EASD) to recommend similar HbA1c guidelines to prevent DR and DN in both type 1 and 2 diabetes (Nathan, et al., *Diabetes Care*, 31(1):173-5 (2008); Rodbard, et al., *Endocrine Practice*, 14(6):791-5. (2008)).

B. Sample Collection

Methods of collection, storage, and processing of samples are all important, since improper handling can lead to artifactual sample oxidation. Many AGEs measured in stored plasma samples are stable over multiple years. Acceptable stability has been confirmed by observing similar levels of analytes, when we compared levels in plasma samples stored at −80° C. for 10-15 years with those in freshly drawn plasma from diabetic subjects.

During sample preparation, it is important to take steps to prevent formation of artefacts. For example, rapid separation of red blood cells from plasma at 4° C., use of chelating agents such as EDTA in blood sample, addition of a preservative or antioxidant such as Butylated hydroxytoluene (BHT), immediate snap freezing such as on dry ice, and storage at −80° C. are examples of steps that can be taken to minimize formation of artefacts.

In the preferred embodiment, plasma samples that had been are collected by a carefully defined protocol, by collecting in EDTA, immediate spinning to sediment red blood cells (RBCs), separating plasma from RBCs at 4° C., followed by immediate freezing and long-term storage at −80° C. Using this process, MetSO levels were in the expected range when compared with the same samples that showed artifactual OS in serum. None of these modifications were observed in urine samples that were collected and stored by standard protocols.

Based on these observations, plasma is a better choice for measurement of OP and AGEs in stored samples since it contains the chelating agent (EDTA) and is immediately spun and separated from RBCs after collection, and flash frozen. Serum, on the other hand, has to undergo clotting at room temperature before separation and storage, thus exposing proteins to leukocyte myeloperoxidase and other pro-oxidant enzymes. Serum also contains no chelator of trace metals (Fe and Cu), both of which can promote spontaneous in vitro oxidative stress.

A plasma sample is collected from a subject diagnosed with DM and the levels of one or more of the biomarkers are determined. The preferred sample is a plasma ultrafiltrate. This "free fraction" can be prepared by centrifugation at 4° C. through microspin filters (10,000 MW filter cut-off, 50 μl aliquot). The rational for measuring this fraction is because cells maintain the quality and functional integrity of proteins by degradation and replacement of proteins damaged by oxidation and glycation (Thornalley, et al., *Biochemical Journal*, 375(Pt 3):581-92 (2003) and Goldberg, et al., *Nature*, 426(6968):895-9 (2003)). This occurs by proteolysis, liberating the oxidized, glycated, and nitrated, amino acids as free adducts, which in turn are released into blood plasma and excreted in urine (Thornalley, et al., *Biochemical Journal*, 375(Pt 3):581-92 (2003)). Since these free adducts are released into blood plasma as tissue breakdown of AGEs occurs, changes in plasma concentrations reflects tissue damage in diabetes, while providing new markers indicative of the damaging effects of hyperglycemia.

Adduct residues chemically react with and become bound to plasma proteins: Since some of the products are acid labile, chemically bound products are determined after exhaustive sequential enzymatic digests using suitable enzymes. Examples of enzymes that can be used include, but are not limited to, pepsin, Pronase E, Aminopeptidase and prolidase. Methods for digesting product chemically bound to plasma proteins are described in Ahmed, et al., *Biochemical Journal*, 364(Pt 1):1-14 (2002).

The biomarkers in the urine are preferably measured from a urine filtrate, prepared by centrifugation at 4° C. through microspin filters (10,000 MW filter cut-off). Methods for preparing a urine filtrate are described, for example, in Ahmed, et al., *Diabetologia*, 48:1590-1603 (2005).

Methods for the concurrent quantitative measurement of biomarkers indicative of protein glycation, oxidation, and nitrosative damage can utilize a system such as an Agilent Model 6410 Triple Quadrupole MS System with 1200 Rapid Resolution LC System. The HPLC is performed with a modified prior multicolumn method, by utilizing a single 2.0×250 mm Synergy 4 micron 80 A column (Phenomenex, USA) with a mobile phase of Methanol/$H_2O$ gradient with 0.29% heptafluorobutyric acid for ion pairing. This methodology has a total run time of 60 min. The method does not have the sensitivity to accurately measure tyrosine based OPs in plasma filtrate samples A system such as an Agilent Model 6490 Triple Quadrupole MS System with a 1290 Infinity LC System for Ultra high pressure liquid chromatography (UHPLC) (Wilmington, Del.) provides a 1000 fold increase in analytical sensitivity over our previous instrument, and a four-fold improvement in sample throughput.

HPLC methodology using ion pairing can be used to resolve the complex mixture of compounds, but it does have several drawbacks. Ion-pairing agents tend to cause difficulties with HPLC pump performance and constant vigilance and frequent pump washing is needed to keep the system working properly. Ion-pairing systems require long re-equilibration times making it more difficult to design a high throughput environment. Ion-pairing agents may cause ion-suppression and potential loss of signal of target compounds.

Another methodology is hydrophilic interaction chromatography (HILIC), which has recently become an accepted new separation strategy. Like normal phase chromatography, the order of elution for compounds is reversed with the more hydrophobic compounds eluting early and the more hydrophilic compounds being retained in the column, providing several advantages including enhanced retention of the hydrophilic compounds that are present in the mix of compounds and unique selectivity that may help resolve some of the previously co-eluting peaks. Buffers used in this system are ideal for MS/MS detection (low backgrounds and ion suppression). Changing pH of the system can give an alternate method for modifying the selectivity of the system. The columns are now available in the advanced core-shell technology or UHPLC configurations, which are very amenable to high throughput applications, including Agilent Porous Shell Technology.

Another system is C18 stationary phases, which have been modified for different selectivities and enhanced retention of polar compounds. Modification of buffer pH with some of these alternate systems should lead to better retention and different compound selectivities. Some examples of this technology include Synergi Polar-RP with an ether linked phenyl group for retention of polar compounds without ion-pairing, or Luna NH$_2$ phase for polar selectivity and a weak anion exchange capability, which could be utilized at a higher buffer pH to increase retention of polar compounds.

Mixed-mode stationary phases are very new to HPLC. These columns combine C18 and ion exchange capabilities into one column. Many times the ion-exchange capability can mimic the effects of an ion-pairing agent. A mixed mode column with cation exchange capability should also be useful.

C. Biomarker Assay and Determination of Risk for Developing DN

In a preferred embodiment, the level of biomarkers in the plasma and urine prepared as discussed above are determined by Liquid Chromatography/Triple Quadrupole Mass Spectroscopy (LC-MS/MS). Utilizing methods involving carefully modified conditions, the biomarkers can be measured utilizing internal standardization by stable isotope substituted standards.

To determine the optimal sample number required to provide a representative estimate of each of the plasma and urinary biomarkers over time, multiple measurements were used to calculate an acceptable quantitative estimate of each analyte. A representative calculation by this approach follows based on urinary pentosidine levels in 4-6 samples/diabetic subjects for ten subjects, over 5 years. For these measurements, it was determined that between person variance=$7.64 \times 10^{-7}$ and within person variance=$2.06 \times 10^{-6}$. Thus Total Variance=Between person variance+Within person variance=$7.64 \times 10^{-7} + 2.06 \times 10^{-6} = 2.82 \times 10^{-6}$. For the mean of N observations from the same person, the Variance of Mean would then=Between person variance+Within person variance/N or $7.64 \times 10^{-7} + 2.06 \times 10^{-6}/N$.

Based on these calculations, one can then determine if the within person variance of the mean is less than the between person component. As shown in the table above N=3 will achieve this aim since $2.06 \times 10^{-6}/3 = 6.87 \times 10^{-7}$ which is less than the $1.45 \times 10^{-6}$ variance of mean value ($3^{rd}$ line in table). For sample sizes more than four, little is gained in these studies by increasing the number of analyses since each additional observation gives <5% total reduction from a sample size of 1.

A database has been compiled of the levels of the various biomarkers that are indicative of the patients at risk of developing kidney disease or other complications. Non-diabetic levels are about ⅓ to ¼ of those seen in diabetics, as shown in Table 1. In one embodiment, levels of CEL <0.042 (0.020-0.042), MGHI <0.103 (0.030-0.103) and CML <0.062 (0.033-0.062) indicate a 94% chance that the individual is protected from DN (in the lower tertile of change).

The levels of the three products were significantly higher in the fast progressors (upper quartile of GBM change) relative to the non-progressors. This analysis was performed by a Wilcoxon method.

TABLE 1

AGEs as Early Indicators of DN

| Biomarker (All nM) | FP Mean ± SD | SP Mean ± SD | P-Value (Wilcoxon) |
|---|---|---|---|
| CML | 0.088 ± 0.022 | 0.075 ± 0.023 | 0.003 |
| MGHI | 0.200 ± 0.099 | 0.165 ± 0.127 | 0.040 |
| CEL | 0.058 ± 0.015 | 0.049 ± 0.015 | 0.026 |

Linear regression analysis of any product or products versus progressive thickening of the GBM (DN progression) shows that the square of the R (correlation coefficient), which is a measure of the degree of prediction for each biomarker, was greater for the three biomarkers with Hbg A1c relative to Hbg A1c alone. For example, in Table 2, HbA1c accounts for 4.7% of predictive value (0.047), CML 0.026%, etc. The sum of the three biomarkers plus A1c was 11.6%. The value of measuring a biomarker one time is additive to A1c.

TABLE 2

Linear Regression of AGEs as Early Indicators of DN

| Variables in Regression Model | % of explained variation (r-squared) | |
|---|---|---|
| | GBM | MES |
| CEL | 0.026 | 0.002 |
| CML | 0.026 | 0.01 |
| MGH1 | 0.006 | 0.005 |
| HbA1c | 0.047 | 0.027 |
| A1c + CEL | 0.073 | 0.029 |
| A1c + CML | 0.065 | 0.034 |
| A1c + MGH1 | 0.051 | 0.031 |
| A1c + CEL, CML, MGH1 | 0.116 | 0.052 |

The other type of analysis is the Logistical Regression analysis which allows one to calculate an odds ratio. This allows one to predict the increase in risk of progression to dN in a linear fashion relative to the level of each product. This is probably the closest to quantitative prediction of risk and as described herein, predicts a 10 to 50% risk.

The lower tertile of values for the three biomarkers showed that for CEL <0.042 (0.020-0.042), MGHI <0.103 (0.030-0.103) and CML <0.062 (0.033-0.062), there was a 94% chance that the individual is protected from DN (in the lower tertile of change).

Each of the three biomarkers are individually predictive of progression to DN in combination with HbA1c, and the sum of the increased predictive power of kidney change (increased GMB width) is increased from 4.7% for one measurement of A1c, to 11.6% for the three biomarkers. This represents an increase of 7.9% which is 2.5 fold or 247% greater than A1c alone.

Figure 2A:
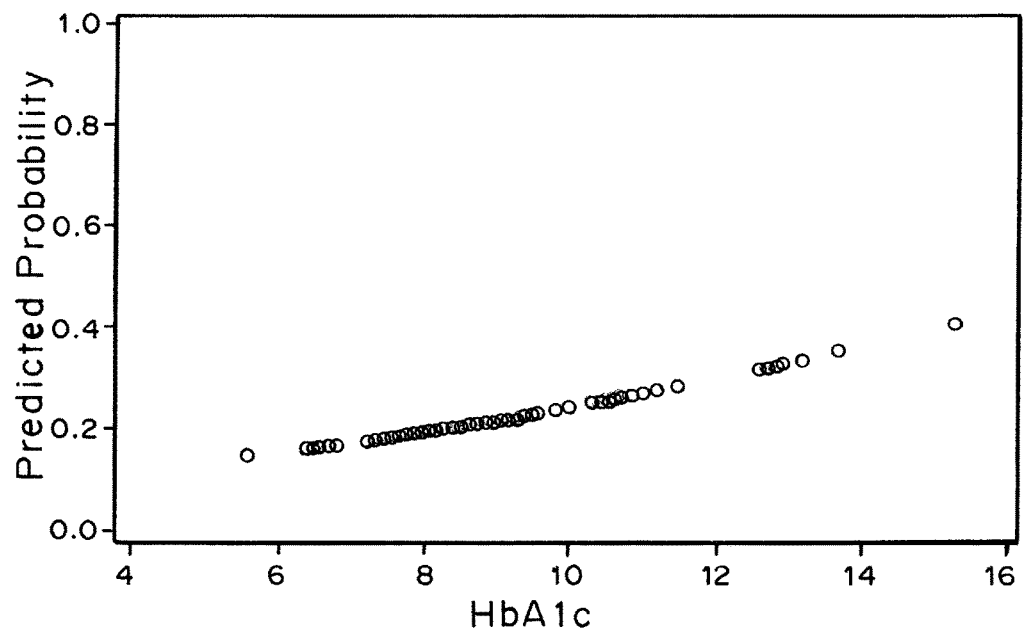
FIGS. 2A-2D. A logistic regression model was used to develop predictive equations relating each biomarker to the probability of a subject's classification as a "fast" progression (FP) of DN. CML and MGH1 values were log transformed when used as predictors and then back-transformed when creating predictive probability plots. For the 3 biomarkers, but not for $HbA_{1C}$ (p=0.28) measured at the same time, there was a significant relationship to the probability of classification as a FP (CML p=0.02; CEL p=0.03; MGHI p=0.048). For HbA1c, the relationship was significant when fit to the entire sample (n=186) over 5 years (p=0.006).
Figure 2B:
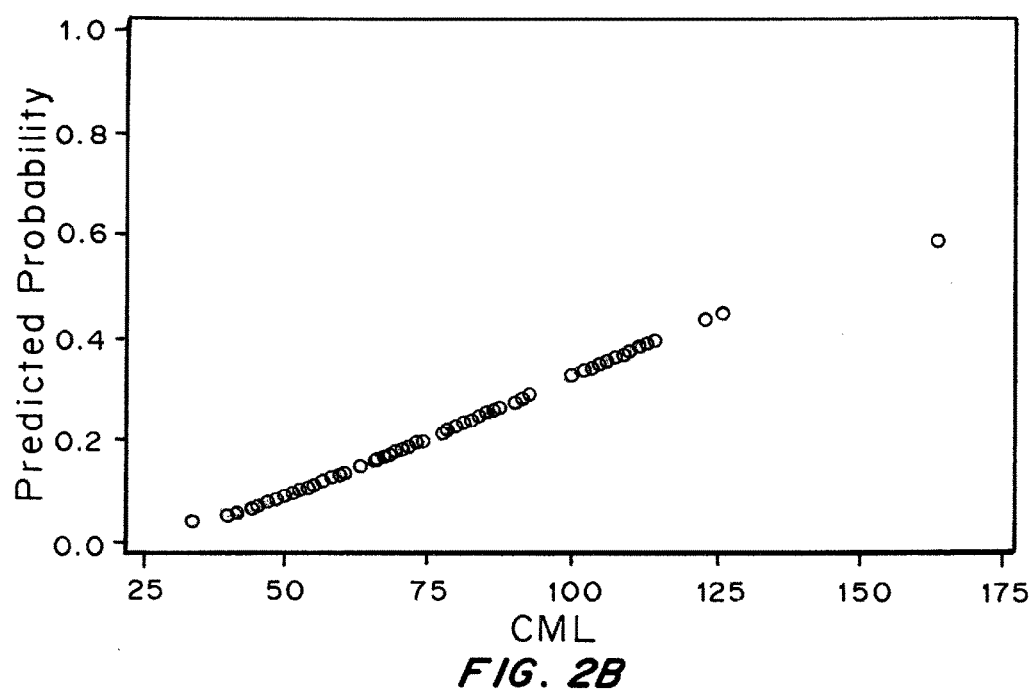
Figure 2C:
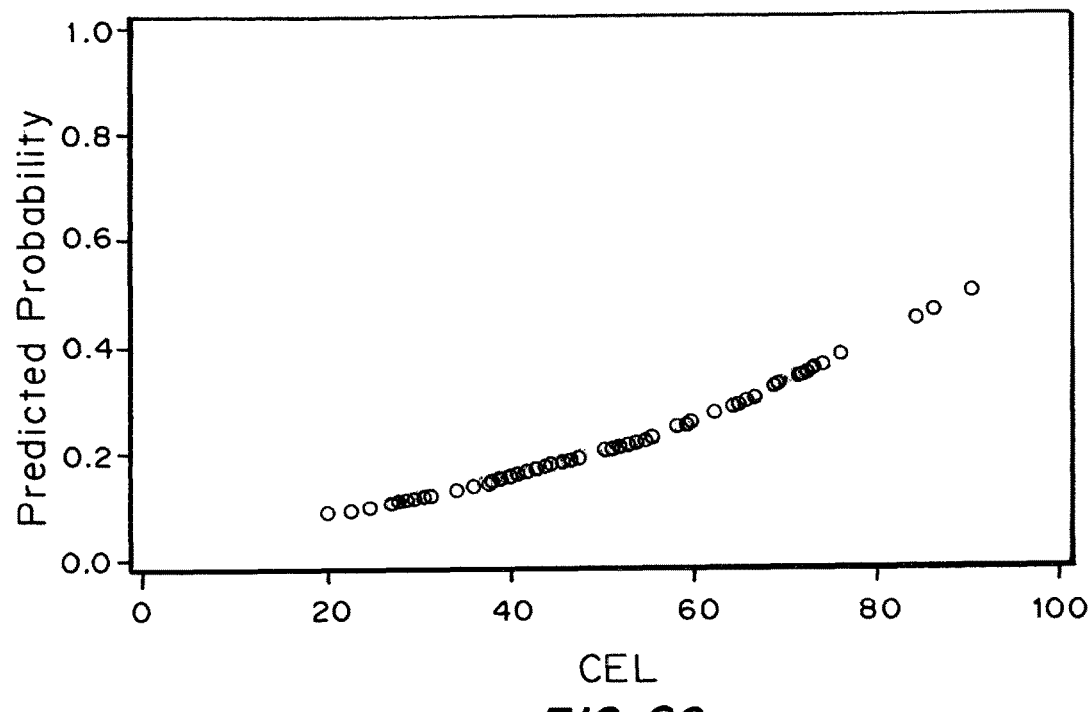
Figure 2D:
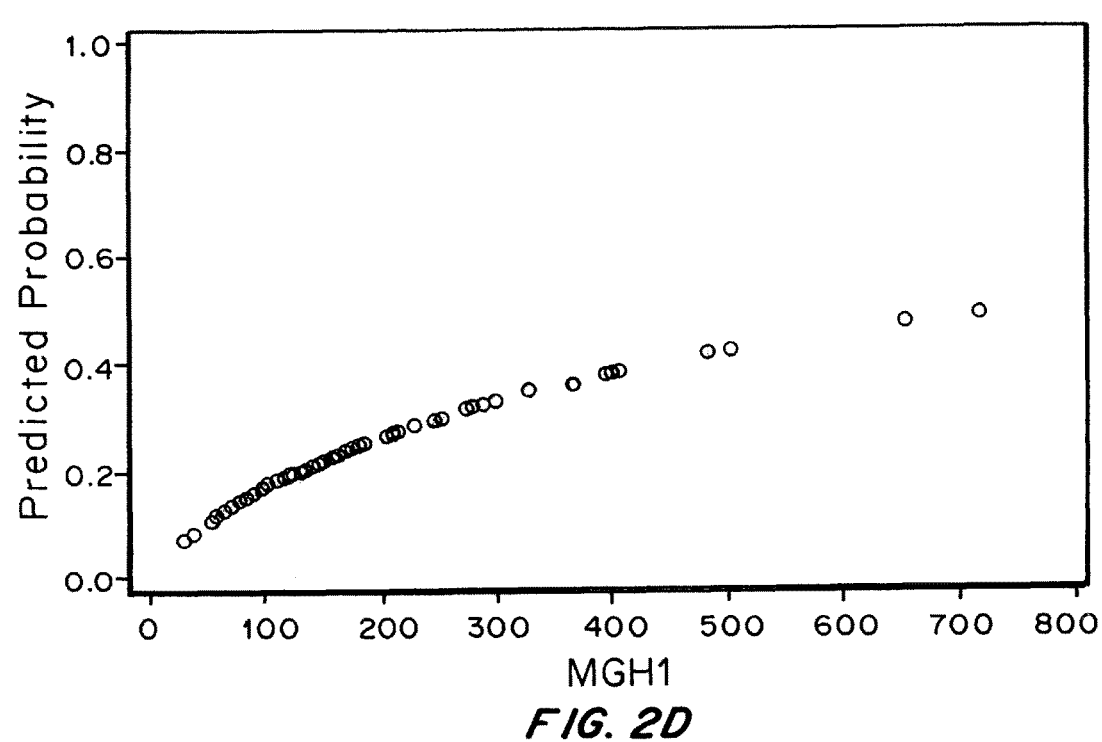

Analyses performed by logistical regression show the odds of progression of DN (y axis) relative to the levels of the 3 biomarkers (X axis) (FIGS. 2B-D), relative HbA1c (FIG. 2A).

The Odds ratio for progression for CEL, MGH1 and CML biomarkers is 68 to 92% for each one standard deviation of change is provided in Table 3, below.

TABLE 3

Odds Ratios for Prediction of Rapid Progression of DN by $A_{1c}$ or AGEs

| Biomarker | Odds Ratio | 95% Confidence Interval | Value of 1 SD Change |
|---|---|---|---|
| HbA1C | 1.29 | (0.82, 2.02) | 1.74 |
| CML (log) | 1.95 | (1.14, 3.35) | 0.0157 |
| CEL | 1.72 | (1.06, 2.77) | 0.303 |
| MGH1 (log) | 1.68 | (1.004, 2.81) | 0.561 |

Ten native and internal stable heavy isotope substituted AGE and OP standards were procured from commercially available sources, or by custom synthesis, to create a database. Commercially available standards include Carboxymethyl Lysine (CML), Carboxyethyl Lysine (CEL), Glyoxal Hydroimidazolone (G-HI), Methylglyoxal Hydroimidazolone (MG-HI), and 3-Deoxyglucosone Hydroimidazolone (3DG-H). Oxidative end products (OP) include Methionine Sulfoxide (MetSO), 3-Nitrotyrosine (3-NT), 2-Aminoadipic acid (AAA), and Dityrosine.

These precision diagnostic tests assess an individual diabetic patient's risk of developing specific complications associated with their disease. These precision diagnostic tests are preferably performed on blood samples submitted to a central clinical laboratory facility. In the preferred embodiment, the tests identify the presence and amount of 10 AGEs and OPs biomolecules (biomarkers). A risk profile for the development of diabetic complications, based on a comparison with data obtained from individuals without disease, as well as at various confirmed stages of disease, is constructed. This information is sent to the ordering physician to deliver improved care by specifically adjusting treatments to an individual patient's profile. With increasing focus on individualized, cost-effective treatment plans for patients, access to this information with become increasingly valuable and necessary in the marketplace.

III. Method of Diabetic Care

The methods described herein allow selection of risk and cost appropriate therapeutic regimens for diabetic individuals to achieve appropriate levels of glycemic control and delay or prevent associated DN complications. These biomarkers have more than three times the predictive value for renal complications of the current "gold standard," the Hemoglobin A1C. There is strong scientific evidence that these and other identified biomarkers could be early predictors of propensity to retinopathy, vascular disease, and risk of heart attack and stroke. Diagnostic tests that predict early progression of these complications before symptoms are visible allow doctors and patients to make individual adjustments in treatments and behavior that could significantly improve outcomes. Enhanced outcomes will improve lives, and could save billions of health care dollars annually.

The current paradigm for diabetes care is one of "one size fits all." Parameters are set for all patients, and aggressive specialized treatments are offered either to those who can pay for them or for those who are already experiencing significant complications. The treatment of diabetes is often done with tests that provide retrospective information about what has already happened, followed by "catch up" treatments to deal with problems, rather than proactive individualized treatments to prevent those that are to come. Although aggressive diabetes treatments that are required for highly susceptible individuals can be cost effective in the long run, they are sometimes more expensive in the short run, and are likely to be accompanied by a higher risk of hypoglycemia and drug side effects. Therefore early identification of high-risk individuals is necessary to balance the potential benefit against the increased risk and expense of new pharmacologic agents and newly evolving high-tech treatments. The glycation/oxidation based diagnostic assays should significantly change preventative interventions by allowing the identification those at high or low risk of diabetic complications during the earliest stages of diabetes. Risk and cost appropriate therapeutic regimens can then be implemented to achieve appropriate levels of glycemic control. For example, those identified as being most susceptible to complications could have more stringent goals for glycemic control than is generally achieved (A1c<6.0%), by initiating intensive insulin delivery and monitoring systems, pancreatic transplants or the artificial pancreas closer to diabetes onset. These risky goals could be justified by the observation that individuals with blood sugars this close to normal, do not develop diabetic complications irrespective of genetic predisposition.

Early more aggressive treatment of other vascular risk factors, or specialized diets with low levels of AGEs, could also be considered. Considering the high risk profiles of individuals detected with the testing, different guidelines for risk of new therapeutic agents may also be justified. The development of therapeutic approaches that could block offending toxic chemical pathways to delay or arrest complications could also be stimulated by information provided by these studies on basic biochemical mechanisms and pathways responsible for diabetic complications.

In other embodiments, these individuals could be administered medications that modify the renin-angiotensin system (Mauer, et al., *Journal of the Renin-Angiotensin-Aldosterone System*, 3:262-269 (2002)), cholesterol and VLDL levels can be initiated (Almuti et al., *International Journal of Cardiology*, 109(1):7-15 (2006); Degenhardt, et al., *Cellular & Molecular Biology*, 44(7):1139-45 (1998); Rosario, et al., *Current Diabetes Reports*, 6(6):455-62 (2006)). Alternatively, or in addition, specialized diets with low levels of AGEs or oxidative products (Koschinsky, *Proc. Nat. Acad. Sci. USA*, 94(12):6474-6479 (1997)) can be used. Important information provided by these studies on basic biochemical mechanisms and pathways responsible for diabetic complications could also stimulate development of therapeutic approaches that could modify offending toxic chemical pathways to delay or arrest DN, DR, and CVD.

Examples of drugs that can be used to modify diabetes management based on the subjects risk of developing DN include, but are not limited to, Metformin (Beisswenger et al., *Diabetes and Metabolism*, 29:6S95-6S103 (2003); Beisswenger, et al., *Diabetes*, 48:198-202 (1999)); Aminoguanidine (Lo, *Amino Acids*, 5:172 (1993); Hirsh, J et al., *Carbohyd. Res.*, 232:125-130 (1992); Brownlee, et al., *Diabetes Care*, 15(12):1835-43 (1992); Hammes, et al., *Proc. Nat. Acad. Sci.*, 88:11555-11558 (1991); Thiamine and Benfotiamine (Hammes, et al., Nature Med., 9(3):294-299 (2003).

Levels of biomarkers of glycation and oxidative stress are risk factors for the rate of development and progression to advanced diabetic retinopathy(DR) and nephropathy(DN) over time. Levels of glycation and oxidative stress biomarkers are also risk factors for the ultimate development of cardiovascular disease (CVD) in Type 1 diabetes. The effects of biochemical biomarkers of glycation and oxidation on defined outcomes can be assessed using a case-cohort design involving DR, DN and CVD cases and controls. For each selected subject, blood plasma and urine samples obtained at multiple specified times are employed, for example, DCCT randomization; DCCT one year visit; DCCT closeout (=EDIC baseline); and EDIC year one. This will provide adequate sample numbers and distribution to be representative of each biomarker.

This can be used to assess the risk factors for the progression of microvascular and cardiovascular disease in type 1 diabetes. The three primary outcomes are the development of advanced retinopathy; (proliferative diabetic retinopathy (PDR) detectable via fundus photography or the requirement for pan-retinal photocoagulation (laser)), nephropathy; (the development (macro) albuminuria (>300 mg albumin/24 h) or end-stage renal disease (ESRD)); and the occurrence of a cardiovascular disease event. Albumin excretion rate is assessed from a four hour timed measurement of albumin excretion rate annually during DCCT and every other year (half/year) during EDIC. The composite cardiovascular outcome includes fatal or non-fatal myocardial infarction or stroke, ischemic angina, revascularization, or silent MI detected on an annual ECG.

A case-control design provides an efficient method to test the above aims for each of the three outcomes (case definitions). However, a simple random sample of controls from among those event-free at the end of the trial would be biased owning to a longer average duration of exposure than the cases. A nested case-control study avoids this bias by randomly sampling controls from among those at risk at the time each selected case is observed. The data is then analyzed using a conditional regression model stratified by case-control set, or equivalently, a like-stratified Cox proportional hazards model. For each outcome, 125 cases with 250 controls will provide 85% power to detect an odds ratio of 1.39 per SD difference at the 0.05 level two-sided. With three separate case definitions, three separate nested case-control sub-studies could require up to 3×375=1125 subjects. Alternately, a case-cohort approach can be employed in which a single baseline randomly sampled "sub-cohort" is selected from the full cohort to provide a basis for controls for each case definition. The efficiency (power) of this design for given case-control sample sizes are equivalent to that of a nested case-control study of the same size. Thus, a case-cohort design that yields approximately 250 controls for each case definition will provide excellent power to detect meaningful associations of biomarkers with each of these outcomes.

A case-cohort of 350 subjects with a 2:1 ratio of secondary to primary cohort subjects was randomly selected since about twice as many cases of each type occurred in the secondary than primary cohorts. This provided some cases of DR, DN and CVD. Additional cases of each type were selected from the remaining 1091 subjects necessary to obtain at least 125 cases of each type. It was not possible to do so exactly because some subjects who were cases by one criterion were also cases from another. Then, for each case definition, 250 or so controls were sampled. The table provides the numbers of cases and controls within the primary and secondary cohorts, and total that were selected.

TABLE 4

Numbers of Cases and Controls with Primary and Secondary Cohorts.

|  | Total | Primary | Secondary |
| --- | --- | --- | --- |
| CVD | 381 | 159 | 222 |
| Cases | 127 | 53 | 74 |
| Control | 254 | 106 | 148 |
| PDR | 375 | 108 | 267 |
| Cases | 125 | 27 | 98 |
| Control | 250 | 81 | 169 |
| Albuminuria | 375 | 148 | 227 |
| Cases | 125 | 48 | 77 |
| Control | 250 | 100 | 150 |

Since many cases and controls for one outcome are also cases or controls for another outcome, the total study with three sets of cases and controls comprises a total of only 546 subjects, 200 from the primary prevention cohort and 346 from the secondary intervention cohort. It includes all cases of CVD observed at the time the sample was drawn and random samples of 125 of the DR and DN cases observed at that time. For each of the three case definitions, a modification of the Cox proportional hazards model for case-cohort sampling will be used to assess the relative risk per SD of the biomarkers at each time when added individually to models with and without corresponding longitudinal measures of $HbA_{1c}$. Models will also adjusted for primary/secondary cohort, duration of diabetes on entry and the entry level of $HbA_{1c}$. Models will be fit using just the baseline levels of a biomarker and then also using the values of the biomarker at the three additional time points as a time dependent covariate. The latter will be used to assess whether the baseline biomarker alone confers additional risk independently of the longitudinal $HbA_{1c}$.

Models can also be used to evaluate the effects of the set of biomarkers jointly. Before doing so, collinearity diagnostics will be applied to ensure that there is not a degree of linear dependence (inter-correlation) that leads to variance inflation in the estimates. If so, within each group of related markers, the one with the strongest effects will be employed jointly with those from other groups. A likelihood ratio test will then assess whether the final set of biomarkers contributes significantly to a model that also contains the longitudinal $HbA_{1c}$ values.

The present invention will be further understood by reference to the following non-limiting examples.

Example 1. The Relationship Between Plasma Levels of AGEs and OPs and Nephropathy Progression/Non-Progression Materials and Methods Instrumentation:

HPLC—Agilent 1200 Series Binary Pump, Autosampler, Degasser and Thermostatted Column Chamber; QQQ-Agilent 6410.

Materials:

MS grade water and methanol are from Honeywell.

Heptafluorobutyric acid (HFBA) LC grade, Fisher, (Pierce Chemical) # PI-53104

HPLC Column—Gemini-NX 3u C18, 4.6 mm×250 mm Phenomenex #00G-4453-E0.

Since the analysis of 9 proposed biomarkers by LC-MS/MS is done on a single run, and requires the addition of heavy isotope internal standards for accurate quantification, the required light and heavy standards for nine biomarkers were obtained as follows: Light and heavy ($N^{15}$) 3DG-HI was obtained from Organix in Essex UK. Heavy MG-HI and G-HI, was produced by NeoMPS in France. Methionine sulfoxide and dityrosine were synthesized, and light and heavy standards of the remaining 5 biomarkers (Pentosidine, CEL, CML, MGHI and GH) were purchased from available commercial sources. 2-amino adipic acid, a stable lysine derived end product which is an excellent indicator of oxidative stress was obtained from Sell and Monnier at Case Western Reserve University in Cleveland Ohio. (Beisswenger, et al., *Diabetes,* 54:3274-3281 (2005)). The addition of heavy isotope internal standards for accurate quantification is required since the analysis of these 9 proposed biomarkers by LC-MS/MS is done on a single run.

Methods:

Measurement of Biomarkers:

The methods developed for the concurrent quantitative measurement of biomarkers indicative of protein glycation, oxidation, and nitrosative damage (Ahmed, et al., *Biochemical Journal,* 364(Pt 1): 1-14 (2002) were modified by employing a single 2.0×250 mm Synergy 4 micron 80A column (Phenomenex, USA) with a mobile phase of Methanol/$H_2O$ gradient with 0.29% heptafluorobutyric acid on the Agilent Model 1200 HPLC, with a total analysis time of 60 min on an Agilent Model 6410 triple quadrupole Mass Spectrometer (QQQ), and approach not used in the art in measuring AGEs or oxidation products.

An important change in this protocol relative to known methods for measuring AGEs is the completely different stationary phase used i.e., C18 (i.e., the Synergy 4 micron 80A column). This column change resulted in use of mobile phase conditions which differ from prior art methods i.e., the use of heptafluorobutyric acid as an ion pairing agent. The combination of column type and mobile phase also allowed the sample analysis to be performed with a single column relative as opposed requiring 2 columns i.e., samples could successfully be run using one column-two columns were not required.

The HPLC and QQQ conditions are shown below.
HPLC Conditions:
Mobile Phase: Solvent A=95% 0.29% HFBA in water/5% 0.29% HFBA in methanol. Solvent B=0.29% HFBA in methanol. Flow rate=0.25 ml/min
Pump Time Table:

| Time | Solvent Ratio B |
|------|-----------------|
| 0    | 0               |
| 3    | 0               |
| 6    | 13              |
| 25   | 29              |
| 35   | 100             |
| 45   | 100             |
| 50   | 0               |
| 70   | 0               |

Column Temperature: 28° C.

QQQ Acquisition Parameters:
The Agilent 6410 MS/MS, equipped with an ESI source was operating in the positive mode under the following conditions: Drying gas was at 350 C with a flowrate of 10 L/min. Nebulizer pressure was 40 psi and capillary voltage was set for 4000 for all compounds. Detailed compound analytical parameters are shown in Table 4.

Using isotopic dilution analysis quantitation of samples was achieved by reading from calibration curves derived from relative response vs. relative concentration to the heavy standard. Heavy standards were added to plasma or urine filtrates at final concentrations from 1 to 6 uM in concordance with the expected physiological concentrations and range of the standard curves.

The order of elution of the compounds is as shown in Table 5. This table also shows the coefficient of variation (COV) for repeated between day measurements of the analytes, as well as the lower limit of detection (LLOD) and lower limit of Quantitation (LLOQ) for each analyte.

TABLE 4

Compound Analytical Parameters for Mass Spectrometry

| Compound[1] | Transition | Fragmentor V | Collision V |
|---|---|---|---|
| CML (Quantifier)[2] | 205.1-84.1 | 100 | 22 |
| CML (Qualifier)[2] | 205.1-130.1 | 100 | 8 |
| d4 CML (Isotope)[2] | 209.1-88.1 | 100 | 22 |
| CEL | 219.1-84.1 | 100 | 22 |
| CEL | 219.1-130.1 | 100 | 8 |
| d4 CEL | 223.1-88.1 | 100 | 22 |
| MetSO | 166.1-74.1 | 80 | 7 |
| MetSO | 166.1-102.1 | 80 | 10 |
| d3 MetSO | 169.1-74.1 | 80 | 7 |

TABLE 4-continued

Compound Analytical Parameters for Mass Spectrometry

| Compound[1] | Transition | Fragmentor V | Collision V |
|---|---|---|---|
| 3-NT | 227-181 | 94 | 8 |
| 3-NT | 227-117 | 94 | 20 |
| 6C[13] 3-NT | 233-187 | 94 | 8 |
| MG-H1 | 229-166.1 | 104 | 13 |
| MG-H1 | 229-114 | 87 | 12 |
| d3 MG-H1 | 232.1-169.2 | 104 | 13 |
| MG-H2 | 229-116 | 87 | 12 |
| MG-H2 | 229-114 | 87 | 12 |
| d3 MG-H1 | 232.1-169.2 | 104 | 13 |
| MG-H3 | 229-114.1 | 87 | 12 |
| MG-H3 | 229-116 | 87 | 12 |
| d3 MG-H1 | 232.1-169.2 | 104 | 13 |
| DiTyr | 361.1-315.1 | 100 | 10 |
| DiTyr | 361.1-254.1 | 100 | 18 |
| 2C[13] DiTyr | 363.1-316.1 | 118 | 12 |
| G-H1 | 215-152 | 80 | 9 |
| G-H1 | 215-116 | 80 | 5 |
| 2C[13] G-H1 | 217.2-154.1 | 104 | 12 |
| G-H2 | 215.1-116.1 | 80 | 5 |
| G-H2 | 215.1-100.1 | 100 | 10 |
| 2C[13] G-H1 | 217.2-154.1 | 104 | 12 |
| G-H3 | 215.1-100.1 | 100 | 10 |
| G-H3 | 215.1-116.1 | 80 | 5 |
| 2C[13] G-H1 | 217.2-154.1 | 104 | 12 |
| 3DG-H | 319.1-204.2 | 120 | 14 |
| 3DG-H | 319.1-116.1 | 120 | 22 |
| 6C[13]4N[15] 3DG-H | 329.1-208.1 | 120 | 14 |
| AAA | 162.2-98.1 | 52 | 12 |
| AAA | 162.2-144.2 | 52 | 4 |
| d3 AAA | 165.2-101.2 | 55 | 12 |

[1]Capillary voltage was set at 4000 for all transitions
[2]Transitions remain in the same order throughout table

TABLE 5

Validation of Analytical Method

| Compound | Mean (nM)[1] | Between day COV %[1] | LLOD[2] (nM) | LLOQ[2](nM) |
|---|---|---|---|---|
| MethSO | 1610 | 11.2 | 64 | 210 |
| AAA | 1380 | 9.6 | 81 | 270 |
| CML | 110 | 10.1 | 10 | 34 |
| CEL | 62 | 10 | 8.6 | 28 |
| 3DG-H | 450 | 10.9 | 40 | 130 |
| G-H1 | 22 | 11.6 | 3.1 | 10 |
| MG-H1 | 303 | 8.6 | 5.8 | 19 |
| 3-NT | <LLOQ | — | 2.2 | 7.1 |
| DiTyr | <LLOQ | — | 2.9 | 9.5 |

[1]Calculated from replicate injections of a pooled plasma filtrate n = 18
[2]Calculated from the standard deviation of the response (SD) and the slope (S) of calibration curves. LLOD = 3.3(SD/S) LLOQ = 10(SD/S) Values represent the mean of five calibration curves.
$R^2$ value exceeds 0.99 for all calibration curves Source Parameters:
Mode: ESI Positive
Gas Temp. (350° C.)
Methods for Sample Preparation:
Plasma sample preparation: All of the samples used in this study were collected at the 5-year end of study NHS visit by a rigorous protocol, where blood was collected in EDTA containing tubes and immediately iced and centrifuged. Following centrifugation plasma was immediately separated from red blood cells (RBCs) and snap-frozen on dry ice, and subsequently stored at −80° C. until these analyses were performed.

Ultrafiltrates (free adducts): LC-MS/MS analyses were initially performed on the plasma "free fraction", prepared as the filtrate following centrifugation through 10K cut-off Amicon filters.

Adduct residues chemically bound to plasma proteins: Since some of the products are acid labile, chemically bound products are determined after exhaustive sequential enzymatic digests with pepsin, Pronase E, and Aminopeptidase/prolidase (50 μg protein equivalent) under nitrogen, with controls for protease autolysis, as described by Ahmed, et al., *Biochem J.*, 364(Pt 1):1-14(2002). AGE/OP analyses were performed following extensive sequential plasma digestion over 36 hours with 3 proteolytic enzymes under a nitrogen atmosphere (Ahmed, et al., *Diabetologia*, 48:1590-1603 (2005)) to investigate the protein "bound" fraction.

Urine sample Preparation: For analysis of the biomarkers in urine, 4 samples per subject distributed over the 5 year NHS study, were tested.

Preparation of urine samples to measure excretion of adducts: For determination of the AGE and OP biomarker profile in urine, a filtrate prepared by centrifugation at 4° C. through microspin filters (10,000 MW filter cut-off) as described by Ahmed, et al., *Diabetologia*. 48:1590-1603 (2005) were used. Urine creatinine levels can be determined to provide uniform expression of pro duct/creatinine urine analyte content.

LC-MS/MS was performed on the NHS urine samples which provided an initial total population of 107 subjects consisting of nephropathy progressors (n=37), and non-progressors (n=70). The studies were completed (220 (55×4) additional analyses) over a 10-week period, utilizing a throughput of 24 samples per week. The statistical tests were done on the full sample (n=107 subjects) with a two-sided alpha=0.01. The assumption was that the SD in the whole study sample is the same as the sub-sample (N=52).

The urinary and serum "free fraction" determinations also allow the calculation of renal clearance rates of each analyte.

Results

A. Plasma Filtrates (Free Fraction):

Since it is the best early structural predictor of DN clinical progression, change in glomerular basement membrane (GBM) width from baseline to 5 years in the NHS population measured in electron micrographs of renal biopsies, was the primary endpoint. Mesangial fractional volume was also measured. Fast progressors (FP) were defined as the upper quartile (n=24) of GBM thickening and others as slow progressors (SP). AGEs [3-deoxyglucosone and methylglyoxal hydroimidazolones (DG3H1, MGH1)] and carboxymethyl and ethyl lysine (CML, CEL), and oxidation products [methionine sulfoxide and 2 Aminoadipic Acid] were measured by liquid chromatography, triple quadruple mass spectroscopy on 10 K plasma filtrates on 102 samples at year 5. It was found that MGHI, CEL, and CML levels were significantly higher in GBM-defined FP relative to SP. No AGE or OP predicted mesangial expansion in these studies.

Figure 3:
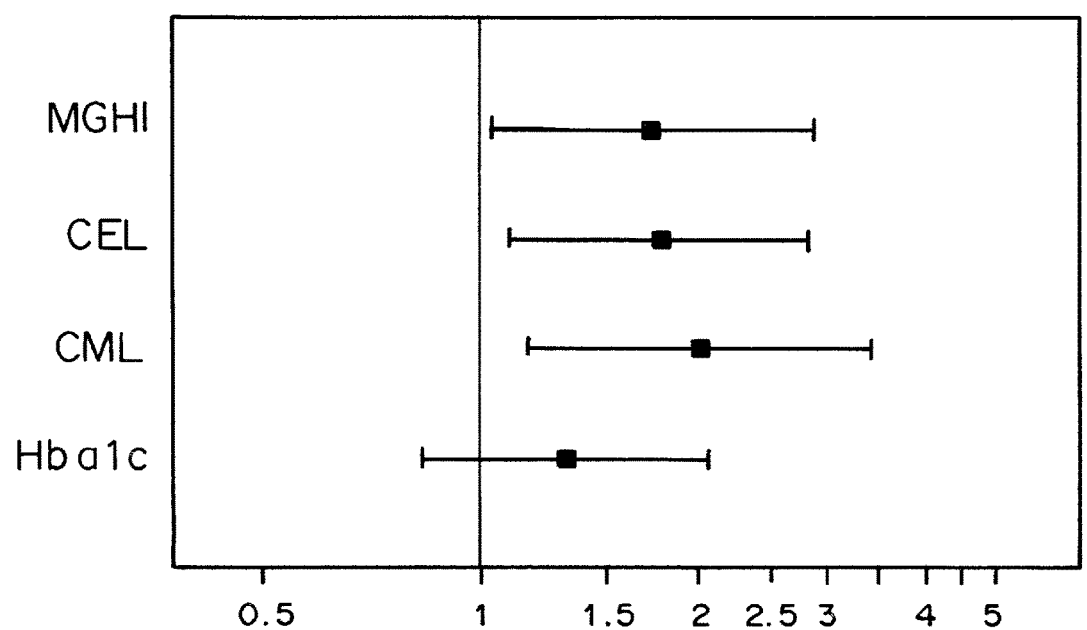
FIG. 3 is a forest plot of the odds ratios (and 95% confidence intervals) for a one standard deviation change in the three informative biomarkers (CML, CEL, and MGHI), and $HbA_{1c}$, as calculated from the logistic regression model. For example, a one SD increase in CEL would lead to a 1.72 increase in the odds of being in the fast progression group. The p values for these plots are associated with those shown in FIGS. 2A-D.

These results show three AGEs (Table 6; FIG. 3), as early indicators of progression of important DN lesions. The other AGE and oxidative biomarkers measured in this study did not correlate with DN progression (Table 5).

TABLE 6

Plasma Biomarker Levels in Fast and Slow Nephropathy Progressors: Based on rates of GBM thickening over 5 years

| Biomarker (All nM) | Fast Mean ± SD | Slow Mean ± SD | P-Value Wilcoxon | Number Progressors/ Non-Progressors |
|---|---|---|---|---|
| CML | 0.088 ± 0.022 | 0.075 ± 0.023 | 0.003* | 22/79 |
| GHI | 0.013 ± 0.001 | 0.013 ± 0.002 | 0.16 | 22/79 |
| MGHI | 0.200 ± 0.099 | 0.165 ± 0.127 | 0.04* | 22/79 |
| CEL | 0.058 ± 0.015 | 0.049 ± 0.015 | 0.026* | 22/79 |
| 3DGHI | 0.382 ± 0.154 | 0.330 ± 0.156 | 0.28 | 22/79 |
| MethSO | 0.931 ± 0.304 | 0.979 ± 0.348 | 0.97 | 22/79 |

Further analyses supporting the value of these three biomarkers in predicting early diabetic nephropathy are the observations that HbA1c at year 5 accounted for 4.7% of the variation in GBM width ($R^2$), but the proportion of variation in GBM width accounted for was increased to 11.6% when MGHI, CEL, and CML were added to the model (7.9% increase). Further, these analyses revealed MGHI as a significant independent predictor of GBM increase.

These findings indicate that MGHI, CEL, and CML are consistently low in those who are protected from progression; thus the biomarkers should identify those protected from DN. The ordered data for MGH1 shows that 2 of 31 (6% OF LOWER TERTILE) MGHI values of fast nephropathy progressors are in the bottom 30% (31 of 103) of the ordered values, but MGHI values of 29 of 31 (94%) slow nephropathy progressors make up this bottom 30%. This was also true of the findings for CEL and CML, where 30 of 32 (94%) of the lowest values were seen in slow progressors for both biomarkers. The levels of these 3 biomarkers were also compared to previously obtained levels for Non-progressors (Ahmed, et al., *Diabetologia*, 48:1590-1603 (2005); Ahmed, et al., *Science*, 44(12):5287-92 (2003)). As shown in Table 7 these studies show that the mean levels for the protected group (DN non-progressors) are similar or slightly higher than levels seen in non-diabetic controls.

TABLE 7

AGEs in Diabetics compared to Non Diabetic subjects

|  | CML | CEL | MG-H1 |
|---|---|---|---|
| #Type 1 diabetes n = 106 | 78 | 51 | 172 |
| ‡Type 1 diabetes n = 21 | 97 | 72 | 331 |
| *Non-diabetic Subjects. N = 6 | 23 | 35 | 110 |
| ‡Non diabetic Subjects | 27 | 25 | 43 |
| Lower Tertile of DN progression n = 32 | 52.4 ± 7.5 | 34.5 ± 6.1 | 71.9 ± 23.2 |

Data from present study
*Data from Ahmed, *Biochem Soc Trans*, 31(Pt 6): 1417-22 (2003)
‡Data from Ahmed, et al., *Diabetologia*, 48: 1590-1603 (2005)

The results show that the level of three AGEs in plasma filtrates (but no OPs), alone or in addition to HbA1c combination, that the three major AGEs, are important predictors (in addition to HbA1c) of progression to DN.

B. Results on Biomarkers in Extensively Digested Plasma Samples to Investigate their Relationship with Progression of DN.

Similar statistical analyses were performed to determine if AGEs and OP (measured on extensive plasma digests of 102 samples, performed as described by Ahmed, et al., *Diabetologia*, 48:1590-1603 (2005), show any correlation with progression of DN defined by GBM thickening or mesangial expansion. Fast progressors (FP) were defined as the upper quartile (n=24) of GBM thickening and the remainder as slow progressors (SP). The same products were measured as performed on the "plasma filtrate" except for 2-amino adipic acid (AAA) which was not measurable on digests, and GHI which was below the limits of detectability. See Table 5. As shown in Table 8 below, there was no correlation between levels of biomarkers in plasma digests and progression of DN.

TABLE 8

Statistical Data for Levels of Biomarkers in Plasma Digest

|  | t-test | Wilcoxon |
|---|---|---|
| CML | 0.62 | 0.75 |
| MethSO | 0.28 | 0.36 |
| 3DG-H1 | 0.61 | 0.50 |
| CEL | 0.70 | 0.61 |
| MG-H1 | 0.22 | 0.30 |

The degree of elevation in protein bound AGEs and OPs were modest, relative to that seen in either plasma of urinary "free" fractions, suggesting less modification of relatively short half-life plasma proteins in diabetes. See Table 9.

TABLE 9

Plasma Hydrolysates Biomarker levels in Plasma in type 1 diabetes and controls

|  | CML | MetSO | 3DG-H | CEL | G-H1 | MG-H1 |
|---|---|---|---|---|---|---|
| DMS NHS samples (Type 1 Diabetes) | 0.031 | 12.8 | 1.03 | 0.0019 |  | 0.024 |
| DMS normal controls n = 8 | 0.024 | 9.94 | 0.93 | 0.0011 |  | 0.022 |

Values expressed as mean mmoles/mole AA

The data in Table 8 shows that none of these protein-bound AGE or OP biomarkers in plasma were related to nephropathy progression or non-progression, based on the degree of GBM change or MES change.

C. Results from Completion of Analysis of Urinary AGEs and Oxidation Products

For these studies, fast progressors (FP) were defined as the upper 37 subjects with the greatest degree of GBM thickening and slow progressors (SP) as the remainder. The analyses were done on the dataset that was corrected for a few outliers where a value was excluded if it was >2 SD beyond that person's own individual mean.

The mean values for the 8 measured biomarkers by Progressor (fast)/Non-Progressor (slow) are shown in Table 10. Of those 8, only urinary levels of CEL (p=0.04) showed a significant difference between groups. CML is next closest (p=0.10), then DiTyr (p=0.16), with all other p-values >0.25. To further confirm these results, the analyses were repeated using non-parametric methods (Wilcoxon Rank-Sum Test), and only CEL (p=0.02) was different between groups. No biomarker correlated with the degree of mesangial expansion over 5 years.

TABLE 10

Urinary Biomarker Levels in Nephropathy Progressors (Fast) and Non-Progressors (Slow)

| grp | N Obs | N | Mean | Std Dev | Minimum | Maximum |
|---|---|---|---|---|---|---|
| Analysis Variable: gh1 ||||||| 
| fast | 35 | 35 | 1.35 | 0.63 | 0.76 | 4.20 |
| slow | 89 | 89 | 1.30 | 0.47 | 0.59 | 3.10 |
| Analysis Variable: dityr ||||||| 
| fast | 35 | 34 | 0.058 | 0.012 | 0.042 | 0.093 |
| slow | 89 | 89 | 0.055 | 0.013 | 0.036 | 0.100 |
| Analysis Variable: mgh1 ||||||| 
| fast | 35 | 35 | 41.4 | 17.6 | 19.2 | 89.4 |
| slow | 89 | 89 | 38.7 | 19.3 | 10.8 | 100.9 |
| Analysis Variable: aaa ||||||| 
| fast | 35 | 35 | 96.9 | 46.9 | 30.9 | 208.5 |
| slow | 89 | 89 | 93.8 | 53.5 | 17.9 | 400.1 |
| Analysis Variable: cm1 ||||||| 
| fast | 35 | 35 | 15.1 | 5.4 | 8.3 | 25.7 |
| slow | 89 | 88 | 13.3 | 5.5 | 5.0 | 30.8 |
| Analysis Variable: methro ||||||| 
| fast | 35 | 35 | 5.54 | 4.09 | 1.23 | 16.43 |
| slow | 89 | 89 | 5.09 | 3.36 | 0.65 | 15.01 |
| Analysis Variable: dgh3 ||||||| 
| fast | 35 | 35 | 51.2 | 18.5 | 23.5 | 89.5 |
| slow | 89 | 89 | 47.5 | 21.9 | 20.2 | 164.2 |
| Analysis Variable: cel ||||||| 
| fast | 35 | 35 | 7.29 | 1.83 | 3.99 | 11.65 |
| slow | 89 | 88 | 6.46 | 2.05 | 2.83 | 13.14 |

Although statistical significance was obtained with CEL, when these results were adjusted for other variables know to effect DN progression, (gender, diabetes duration, age, and HbA1c), these correlations between CEL and DN Progression/Non-Progression were no longer statistically significant (Table 11).

TABLE 11

Univariate and Multivariate analysis of CEL in Urine and GBM thickening

|  | CEL ||
|---|---|---|
|  | Beta | p-values |
| single var (GBM, age adj) ||| 
| Biomarker (CEL) | 1.17 | 0.039 |
| multivariate (GBM, age adj) ||| 
| Biomarker (CEL) | −0.118 | 0.82 |
| HbA1c | 4.43 | <0.0001 |
| Duration | −1.15 | <0.0001 |
| Gender (if F) | −6.45 | 0.0033 |

These outcomes indicate that carefully quantified, specific urinary AGEs and Oxidative biomarkers do not show a statistically significant independent relationship with progression of biopsy proven diabetic nephropathy.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method comprising:
    measuring by Liquid Chromatography/Triple Quadrupole Mass Spectroscopy (LC-MS/MS) the levels of two or more biomarkers selected from a plurality of biomarkers in a plasma sample obtained from a human subject having type 1 diabetes, wherein said plasma sample is purified to provide a purified free plasma fraction;
    adding one or more stable heavy isotope substituted standards corresponding to said biomarkers to said purified free plasma fraction;
    adding one or more ion pairing agents to said purified free plasma fraction;
    further wherein, said plurality of biomarkers comprises methylglyoxal hydroimidazolone (MG-H1) and one or more additional biomarkers selected from the group consisting of $N_\varepsilon$-carboxy methyl-lysine (CML), $N_\varepsilon$-carboxy ethyl-lysine (CEL), and glyoxal hydroimidazolone (GH1); and
    comparing said levels of measured biomarkers to a database of biomarker levels for the same biomarkers previously measured from human subjects, wherein levels of measured biomarkers indicate said human subject's risk of developing diabetic nephropathy.

2. The method of claim 1, wherein biomarker levels of CML, CEL, and MG-H1 are measured in said plasma sample.

3. The method of claim 2, wherein biomarker levels of CEL of less than 0.042 nM, MG-H1 less than 0.103 nM, and CML less than 0.062 nM are measured in said plasma sample.

4. The method of claim 3, wherein biomarker levels of CEL between 0.020-0.042 nM, MG-H1 between 0.030-0.103 nM, and CML between 0.033-0.062 nM, are measured in said plasma sample.

5. The method of claim 1, wherein said purified free plasma sample comprises plasma ultrafiltrate.

6. The method of claim 1, wherein said measuring by LC-MS/MS comprises a stationary phase further comprising C18.

7. The method of claim 1, wherein said human subject is determined to be at risk of developing diabetic nephropathy.

8. The method of claim 1 wherein the individual is determined to be at risk of developing diabetic retinopathy.

9. The method of claim 1 wherein the individual is determined to be at risk of developing diabetic cardiovascular complications.

10. The method of claim 1, further comprising calculating the risk or rate of said human subject developing diabetic nephropathy or a disorder associated with diabetic nephropathy, wherein said risk or rate is calculated based on probability and odds ratios of developing biopsy documented diabetic nephropathy.

11. The method of claim 10, further comprising providing recommended treatment options for said human subject based on the calculated risk or rate of developing diabetic nephropathy or a disorder associated with diabetic nephropathy.

12. The method of claim 11 wherein the treatment options comprise glucose lowering agents.

13. The method of claim 10, further comprising compiling said calculations of said risk or rate of developing diabetic nephropathy or a disorder associated with diabetic nephropathy in said human subject into a report.

14. The method of claim 13, wherein said report is transmitted to a third party or to said human subject.

15. The method of claim 14, wherein said transmitting of said report is done over a network.

16. The method of claim 13, wherein said report comprises a risk profile.

17. The method of claim 13, wherein said report is transmitted to a third party and to said human subject.

18. The method of claim 1 wherein said human subject has not been diagnosed with diabetic nephropathy.

19. The method of claim 1, wherein said one or more ion pairing agents comprises heptafluorobutyric acid.

20. The method of claim 1, wherein a third party obtains said plasma sample from said human subject.

21. A method comprising:
    measuring by Liquid Chromatography/Triple Quadrupole Mass Spectroscopy (LC-MS/MS) the levels of two or more biomarkers selected from a plurality of biomarkers in a plasma sample obtained from a human subject having type 1 diabetes, wherein said plasma sample is purified to provide a purified free plasma fraction;
    adding one or more stable heavy isotope substituted standards corresponding to said biomarkers to said purified free plasma fraction;
    adding one or more ion pairing agents to said purified free plasma fraction;
    further wherein said plurality of biomarkers comprises methylglyoxal hydroimidazolone (MG-H1) and one or more additional biomarkers selected from the group consisting of $N_\varepsilon$-carboxy methyl-lysine (CML), $N_\varepsilon$-carboxy ethyl-lysine (CEL), and glyoxal hydroimidazolone (GH1); and
    comparing said levels of measured biomarkers to a database of biomarker levels for the same biomarkers previously measured from human subjects, wherein said database further comprises kidney biopsy documented progression of diabetic nephropathy, wherein the levels of measured biomarkers indicate said human subject's risk of developing diabetic nephropathy.

* * * * *